United States Patent [19]

Kleinberg et al.

[11] Patent Number: 5,078,129

[45] Date of Patent: Jan. 7, 1992

[54] DEVICE FOR STIMULATING SALIVATION

[75] Inventors: Israel Kleinberg, Smithtown; Leo M. Sreebny, East Setauket, both of N.Y.

[73] Assignee: Research Foundation of State University of New York, Albany, N.Y.

[21] Appl. No.: 490,368

[22] Filed: Mar. 8, 1990

Related U.S. Application Data

[60] Continuation-in-part of Ser. No. 281,103, Dec. 7, 1988, abandoned, which is a division of Ser. No. 45,618, May 1, 1987, Pat. No. 4,820,506.

[51] Int. Cl.$^5$ .......................................... A61M 11/00
[52] U.S. Cl. ........................... 128/200.14; 128/200.21; 128/200.24
[58] Field of Search ............... 128/200.14, 200.23, 128/200.22, 203.15, 200.21, 200.18, 200.24; 424/40, 493; 426/548, 650, 658

[56] References Cited

U.S. PATENT DOCUMENTS

| | | | |
|---|---|---|---|
| 713,017 | 11/1902 | Pumphrey | 128/200.14 |
| 750,521 | 1/1904 | Braymer | 128/200.14 |
| 1,378,481 | 5/1921 | Mobley | 128/200.14 |
| 1,494,809 | 5/1924 | Sahr | 128/200.14 |
| 1,614,532 | 1/1927 | Mobley | 128/200.23 |
| 1,979,006 | 10/1934 | Moran | 128/200.18 |
| 2,212,706 | 8/1940 | Cohn et al. | 128/200.14 |
| 2,362,080 | 11/1944 | Martin | 128/200.14 |
| 2,449,125 | 9/1948 | King | 128/200.14 |
| 2,550,565 | 4/1951 | Hyser | 128/200.14 |
| 2,564,400 | 8/1951 | Hall | 128/200.14 |
| 3,004,718 | 10/1961 | Gorman | 128/200.14 |
| 3,200,817 | 8/1965 | Brainard | 128/200.14 |
| 3,269,389 | 8/1966 | Meurer et al. | 128/200.14 |
| 3,577,516 | 5/1971 | Gould et al. | 128/200.14 |
| 3,666,182 | 5/1972 | Cureton | 239/327 |
| 3,818,908 | 6/1974 | Phillips | 128/200.14 |
| 3,971,377 | 7/1976 | Damani | 128/203.15 |
| 4,157,093 | 6/1979 | Brodsky | 128/200.14 |
| 4,174,712 | 11/1979 | Morén et al. | 128/200.14 |
| 4,820,506 | 4/1989 | Kleinberg et al. | 128/200.14 |

FOREIGN PATENT DOCUMENTS 6600193  7/1966  Netherlands .................. 128/200.22

*Primary Examiner*—Edgar S. Burr
*Assistant Examiner*—Kimberly L. Asher
*Attorney, Agent, or Firm*—Lackenbach Siegel Marzullo & Aronson

[57] ABSTRACT

A dispenser for an aqueous sialogogue for the mouth comprises:

a) a reservoir for the aqueous sialogogue solution;
b) passage means leading from the reservoir to a spray head; and
c) a plurality of orifices in the spray head, whereby actuating the spray head causes a plurality of streams to be directed to those regions of the mouth most dry in a reniform pattern.

Preferably a metered amount of sialogogue is delivered by an actuating means selected from the group consisting of a hand-activating spray pump, a bulb-activated spray pump or an aerosol propellant.

The sialogogue solution comprises:

a) from about 2 to about 3 wgt % of food-grade organic acidulant;
b) a food-grade sweetener benign to stomic microflora; and
c) a saturated calcium phosphate solution, whereby the production of human saliva is promoted in situ without corrosion, infection, or dissolution of human teeth.

15 Claims, 1 Drawing Sheet

DEVICE FOR STIMULATING SALIVATION

RELATED U.S. PATENTS

This application is a continuation-in-part of application Ser. No. 281,103 filed Dec. 7, 1988, now abandoned, which is a divisional application of Ser. No. 45,618 filed May 1, 1987 now U.S. Pat. No. 4,820,506 issued Apr. 11, 1989.

FIELD OF THE INVENTION

This invention relates to xerostomia, or dry mouth. Low generation and flow of saliva in the mouth has several possible causes and substantial effects on taste, eating, digestion and teeth as well as leading to breath malodor, mucositis, sores on tongue, cheeks or lips, desiccation of lips, gingival problems, and microbial imbalance in the mouth. Therefore, stimulation of the generation and flow of saliva can be a great benefit to many people.

It is estimated that about ten percent of the population over 50 years of age and 25 percent of the population over 65 years of age suffer from xerostomia. The majority of those affected are women.

Furthermore, this invention relates to a novel device which is especially adapted to administer on demand a spray of solution to the mouth for stimulating salivation.

BACKGROUND OF THE INVENTION AND PRIOR ART

Some direct primary causes of xerostomia are autoimmune disease such as Sjogren's syndrome, medical irradiation, malnutrition, hormonal imbalance, arthritis and perhaps aging.

When areas of the head or neck are medically irradiated by as little as 1000 rads per week, 85 percent of the patients suffer from xerostomia after six weeks and 95 percent after three months.

Secondarily, xerostomia is a side effect from the administration of over 400 drugs, including major antihypertensives, antidepressants, antispasmodics, diuretics, muscle relaxants, antipsychotics, appetite depressants, and therapeutics for Parkinson's disease.

Furthermore, xerostomia may be emotionally induced by apprehension and fear, but postponed by lascivious anticipation. Breathing through the mouth may also induce xerostomia.

Normally an individual produces 0.5 to 1 liter per day of saliva. Although varying greatly between individuals, on average 65 percent of saliva is submandibular, 23 percent from the parotids, 8 percent from the minor mucous, and 4 percent sublingual. Saliva from the different sources have different proportions of electrolytes such as sodium, potassium, calcium, magnesium, chloride, bicarbonate, and phosphate, as well as nonelectrolytes such as urea and proteins. Upon stimulation, parotid contribution increases and thus proportionally, if not actually, submandibular decreases.

There are two major fractions of saliva, the watery serous portion, which has a lubricative function, and the proteinaceous portion, which has a protective function. Stressful conditions accentuate production of more mucinous saliva from minor glands of the lips, palatal glands, sublingual glands, and to some extent from some submandibular glands. Lascivious anticipation induces more production of the serous component from the parotids and submandibular glands. Patients with serious xerostomia employ synthetic salivary substitutes which supply a more mucinous product.

Food, in general, increases salivary flow. It has been known that the effects of secondary xerostomia may be broadly alleviated by sweet, sour, salty or bitter foods such as sweet candies, lemon drops, peppermint drops, chewing gum, and the like.

Direct sialogogues include:
a) pilocarpine compounds such as the hydrochloride, nitrate, or jaborandi leaves or their extracts;
b) neostigmine and its bromide, distigmine bromide (Ubretid), pyridostigmine bromide (Mestinon);
c) nicotinic acid, nicotinamide (Nicobion 500), and benzopyrone (Venalot); and
d) carbachol (Doryl), potassium iodide, and anethol-trithion (Sulfarlem S 25).

Indirect sialogogues include:
ascorbic acid (Vitamin C), citric acid tablets, malic acid, lemon glycerine swabs, and paraffin wax.

The above information has been reviewed by Imfled in volume 13, number 4, of *Acta Parodontologics* at pp. 1083/111-10996/124 (1984) and by Vissink et al. at volume 129, number 43 of *Ned Tijdschrift Geneesked* at pp. 2054-2057 (1985). Schlatter in U.S. Pat. No. 3,492,131 discloses a family of aspartylphenylalanine esters as synthetic sweeteners about 150 times sweeter than sucrose.

Morris et al. in U.S. Pat. No. 3,584,112 teaches the use of sodium saccharin sweetener to mask the taste of dental plaque-tracing dye solution.

Krasse in "Caries Risk" chapter 8, Quintessence Publ. Co., Chicago, (1985) disclosed an acidulated calcium phosphate-xylitol tablet containing citric and malic acids to be masticated and swallowed each half minute in order to stimulate salivation. Differences in chewing habits would target different salivary glands in different people.

Goodman et al, in European Patent Application 1984—128,654 have disclosed a new class of amino acid based sweeteners: N-(L-aspartyl)-1,1 diaminoalkanes. Goodman's group in *Peptides*, pp. 549–554 (1984) also emphasizes that the bitter taste receptors and sweet taste receptors in the mouth are closely allied, as are the molecular arrangement of "sweet" and "bitter" compounds. These same workers in The Journal of Medicinal Chemistry, volume 27, pp. 1668-1672 (1984) disclose the close relationship between the molecular structure of sweet and bitter trifluoroacetylaspartylanilides.

Of information and belief the authors of the present invention know of no device in the prior art specifically designed for and oriented toward dispensing a sialogogue for the relief of xerostomia.

OBJECTS OF THE INVENTION

It is an object of the present invention to alleviate the symptoms and effects of xerostomia (dry mouth) by stimulating all the salivary glands (submandibular, parotid, sublingual and minor mucous) to produce more saliva simultaneously.

It is a further object of the invention to stimulate salivation cheaply, easily, and graciously without interference with the normal activities of everyday life.

It is yet a further object of the invention to stimulate salivation without burdening the user with any continuous mechanism or activity such as irrigation plates, chewing tablets or gums, repetitive rinsings, or topical application of organic compounds.

It is still another object of this invention to stimulate salivation with a minimum of interaction with human metabolism, that is avoiding the use of drugs or chemicals such as steroids, alkaloids, or aromatics which may have strong side effects or even be toxic in larger doses.

It is an additional object of the invention to stimulate salivation without harming or interacting with the teeth in any way. It is still a further object of the invention to stimulate salivation without swallowing large amounts of saliva or sialogogue.

It is another object of this invention to stimulate salivation by a means which has no psychological or emotional trauma involved.

It is yet a further object to provide a device which allows a patient with xerostomia to alleviate that condition at a variable rate at will.

Still another object is to provide a device for administering a sialogogue in a metered, controlled manner designed specifically in conjunction with the arrangement of the salivary glands in the human mouth and the known relative amounts of saliva and rates of salivation in different parts of the mouth.

Yet an additional object of the present invention is to provide a small, inexpensive, easily manufactured device, which the patient can carry and use at all times to dispense an adjustably metered amount of a sialogogue.

Other objects of the invention will be appreciated by those skilled in the art.

SUMMARY OF THE INVENTION

Surprisingly, the objects of the invention are realized by a dispenser especially adapted by a novel set of orifices to spray an aqueous sialogogue directly onto those areas of the patient's mouth most highly subject to xerostomia.

The novel dispenser comprises a reservoir for the aqueous sialogogue solution, passage means leading from the reservoir to a spray head, and a plurality of orifices in the spray head.

The reservoir and the container for the reservoir are conventional vessels preferably adapted to be held in the hand, and preferably sized to be kept in a pocket, purse, medicine chest, small sports bag, or any other storage space.

The container having the reservoir and conventional passage means, such as but not limited to a tube, may be actuated by any conventional means such as a hand-activated spray pump, a bulb-activated spray pump, or an aerosol pressurized dispensing system. Metering means for controlling the amount of each delivery by either weight or volume is preferred. These metering means are conventional.

The proprietary aspect of the present invention resides in the orifice or orifices in the spray head. Preferably the plurality of orifices or one orifice of custom design dispenses one or more sprays to yield a reniform (kidney-shaped) target area. The reniform target area comprises the central area of the palate, the anterior of the tongue, and the plica sublingualis areas of the mouth, which are direct areas. By driest areas of the mouth most subject to xerostomia, we mean those areas which deliver from zero to about 0.05 microliters per second to a paper measuring strip placed perpendicular to a mouth tissue surface. Also considered dry and subject to xerostomia are the intraoral mandibular lip in the center and the intraoral maxillary lip in the center which provides about 0.05 to about 0.15 microliters per second of saliva. Also in this next to driest areas in the typical human mouth are the anterior areas of the tongue on both sides and the plica sublingularis area at posterior area of the floor of the mouth near the openings from Wharton's ducts.

Those areas of the mouth which secrete from abut 0.2 to about 0.3 microliters per second are less likely to be dry from xerostomia. Most predominant in this range are saliva secreted from Stenson's ducts in the cheek.

The most moist areas of the mouth in tests of 20 white adults are the upper posterior areas of the tongue, the parotid intraoral opening in the cheek, submandibular saliva glands on the anterior floor of the mouth. These areas secrete about 0.3 to about 0.4 microliters of saliva per second. All these areas are shown in FIG. 1 for the mouth and FIG. 2 for the tongue. Table 1 gives the coding for the comparative amount of relative moisture on some of the mucosal sites in the mouth.

The function of the proprietary array of orifices in the spray heads of the dispenser of the present invention is to allay xerostomia in the human mouth. Some proprietary designs for orifices are seen in FIG. 3, wherein sprays of solution emanating from these proprietary array have a reniform shape.

Arrays of orifices in the spray head to give the generally reniform spray which is optimal for relieving xerostomia by occasional or repetitive spraying of sialagogic solution may take many forms. Any form is suitable so long as the shape of the spray (not the orifices) is reniform. Some of the preferred shapes are a flat isosceles triangle, an equilateral triangle, a diamond, a crescent, or a series of holes in crescent array. The crescent or crescent array of holes may or may not have an extra lower hole designed to alleviate the xerostomia of the mandibular lip. Also, a diamond array of holes rather than just an upper triangular array is designed for spraying the mandibular lip.

Further control of the shape and relative delivery of sialogogic solution can be achieved by employing holes of different relative sizes. By no means need all the holes in the illustrative, but not limiting, examples of FIGS. 3a to 3e have the same size. The holes may range from less than 1 mm in diameter to about 10 mm in diameter, or even larger.

DESCRIPTION OF THE PREFERRED EMBODIMENTS

Figure 1:
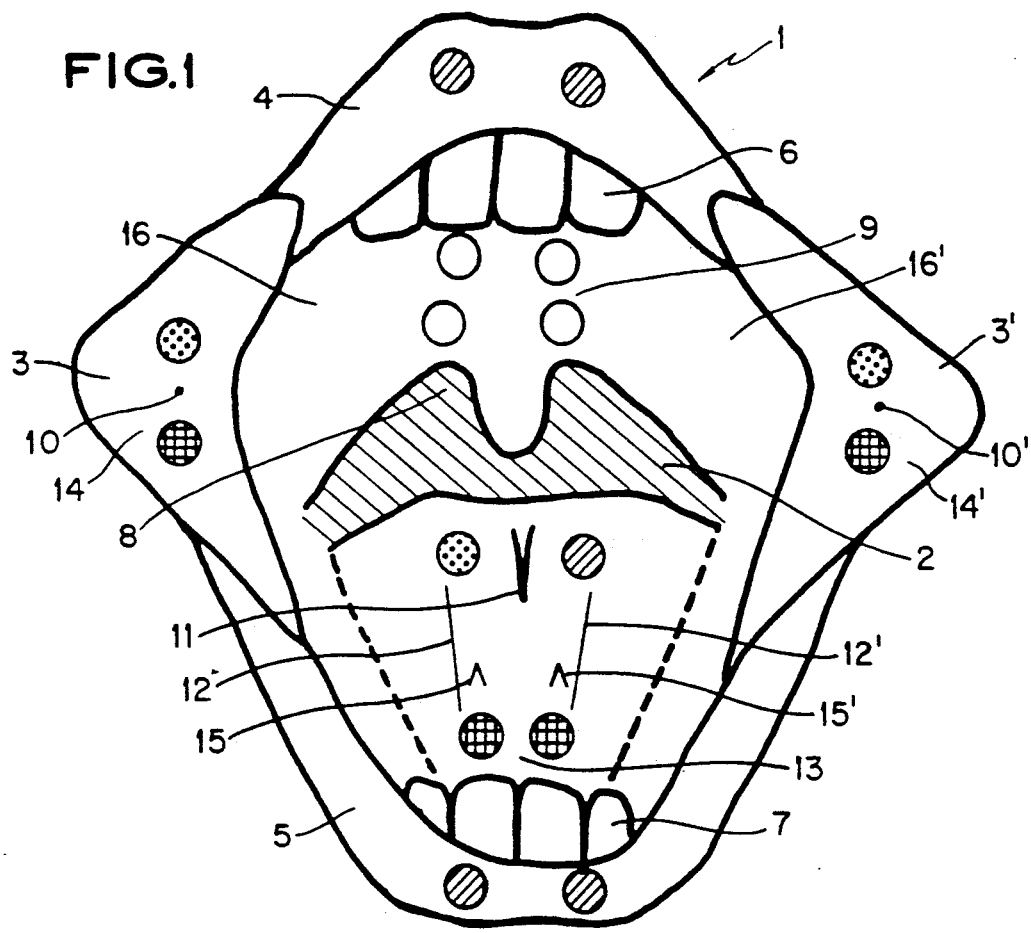
FIG. 1 is a front view of the human mouth.
Figure 2:
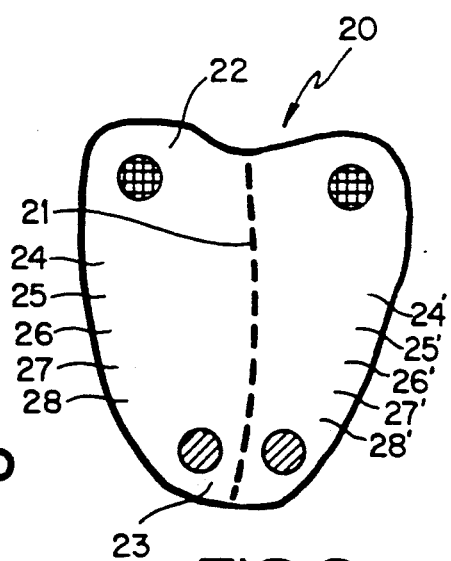
FIG. 2 is a top view of the human tongue.

FIGS. 1 and 2 show the value of minimal equilibrium depth of moisture on some mucosal sites in the mouths of a sample of white adults. The open circles are most prone to xerostomia, since those regions provide about 0 to about 0.05 microliters/sec of saliva. The diagonal circles show areas providing about 0.05 to about 0.1 microliters/sec of saliva. The dotted circles show about 0.1 to about 0.15 microliters/sec, and the cross-hatched circles show saliva values of about 0.15 to about 0.2 microliters per second.

FIG. 1 shows a mouth 1 having a throat 2, cheeks 3 and 3', a maxillary upper lip 4, a mandibular lower lip 5, upper teeth 6, and lower teeth 7.

The uvula 8, the palate 9, the intraoral parotids 10 and 10', the tongue ligament 11, the two plica sublingualis ridges of salivary glands 12 and 12', and the anterior floor of the mouth 13 are also shown.

Stenson's ducts are located at 14 and 14', while the openings from Wharton's ducts, submandibular saliva glands, are located at 15 and 15'. There are palatal mucous glands at 16 and 16'.

FIG. 2 shows a tongue 20, having a central fissure 21, a posterior rear portion 22, an anterior front portion 23, and numerous taste glands along the side represented by 24, 25, 26, 27, 28, and 24', 25', 26', 27', and 28'.

Figure 3A:
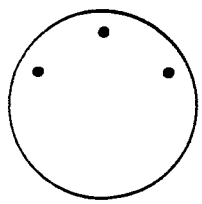
FIGS. 3a, 3b, 3c, 3d, and 3e are illustrative front views of orifices of spray heads which deliver generally reniform sprays for alleviating xerostomia.
Figure 3B:
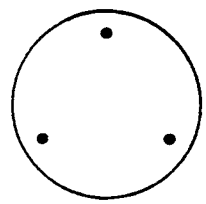
Figure 3C:
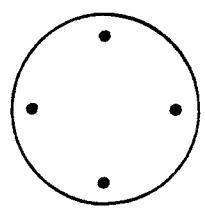
Figure 3D:
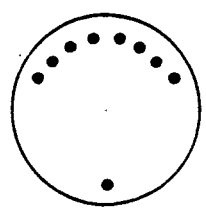
Figure 3E:
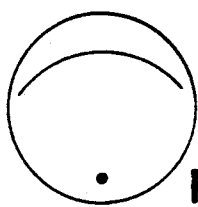

FIGS. 3a, 3b, 3c, 3d, and 3e illustrate but do not limit the front views of representative arrays of spray heads which can yield a generally reniform (kidney) shaped spray which alleviate chiefly xerostomia at the most vulnerable areas of the mouth and tongue, namely those shown with empty or diagonal circles in FIGS. 1 and 2. The numbers of holes in FIG. 3d are illustrative not exact. The exact degree and length of arch in FIG. 3e are illustrative not limiting. The lower orifice in FIGS. 3d and 3e are optional. Of course, if the lower orifice in FIG. 3c is not present, it becomes the same as FIG. 3b. The relative size of all the orifices in all of FIGS. 3a to 3e. to each other and to the spray head are only diagrammatic, not actual. In fact, any orifice can range in size from a fraction of a millimeter to about 10 mm. Other arrays of orifices to achieve a generally reniform (kidney) shape will be obvious to those skilled in the art, after having seen the examples of FIGS. 3a to 3e.

Using an ordinary circular watchface having arabic numerals as a guide, one may say that FIG. 3a has orifices at 10, 12 and 2 o'clock. FIG. 3b has orifices at 9, 12, and 3 o'clock. FIG. 3c has orifices at 9, 12, 3 and 6 o'clock. FIG. 3d has orifices at 10, 10:30, 11, 11:30, 12, 12:30; 1, 1:30, 2 and 6 o'clock. And FIG. 3e has an orifice at 6 o'clock and an arc extending form 10 o'clock to 2 o'clock.

The dispensing means and metering means are conventional and not a part of the present invention. Some of the details of such conventional dispensing apparatus may be seen in the Figures of U.S. Pat. Nos. 3,137,416; 3,148,127; 4,174,811; 4,247,025; 4,001,232; and 4,398,654; 4,466,838; 3,207,386; 3,260,421; and 4,396,152 among others.

The aqueous sialagogic solution may be in bulk form or in the form of an atomized droplet colloidal spray comprising:
a) from about 2 wgt percent to about 3 wgt percent of a food-grade, organic acidulent;
b) from about 0.05 to about 0.5 wgt percent of a food-grade synthetic sweetener or 0.5 to about 25 wgt percent of a food-grade natural sweetener; and
c) a saturated calcium phosphate solution.
whereby the production of all the salivary glands are promoted in the mouth without any corrosion, infection, mottling, discoloration, dissolution, or attack of either natural or prosthetic teeth.

The preferred form of the liquid is that of a metered, atomized, colloidal droplet spray of about 0.15 to 0.5 ml per actuation at a pH of about 3 to 4.

The preferred acidulants are citric, malic, and ascorbic acid of which citric acid is most preferred.

The preferred sweeteners are synthetic of which aspartylphenylalanine (Aspartame) and saccharin are most preferred.

The preferred forms of calcium phosphate are calcium monohydrogen phosphate (dibasic) or monocalcium dihydrogen phosphate (monobasic).

The preferred pH of either the liquid or the spray is from about 3 to about 4.

The onset of the effects of xerostomia is insidious with no clear line of demarcation when one has or has not the malady. Also different individuals may have different symptoms to a differing extent in a different succession. Dry mouth is their most common symptom. Alteration of taste sensation leads to change in the selection and perception of food. After alteration comes taste desensitation, which may lead to lack of any taste.

Sores on any of the mucous tissues of the oral area (tongue, gums, mouth, cheeks etc.), ulcerations, fissures, swellings, bleeding, coatings, even erosion of the tongue are all possible. With the decrease in saliva comes incomplete digestion, buildup of food, plaque, gingival hemorrhage, soreness at dental bridges, and extreme breath malodor. Also possible are swelling of various mouth tissues and possibly difficulty of speech. The lips may become desiccated or cracked. The rate of dental caries may increase dramatically.

One general approach to xerostomia is the use of synthetic saliva. There are many commercial brands, based on either pig mucin or carboxymethylcellulose (CMC), and including all the requisite electrolytes, buffer, and optional flavorants and/or sweeteners. The usual electrolytes are potassium, sodium, magnesium, calcium, chloride, bicarbonate, phosphate, and fluoride. Except for one Danish brand (Saliva-Orthana) and one Dutch experimental type based on mucin, most artificial salivas are based on CMC. VA-ORALUBE (First Texas Labs., Dallas) contains sorbitol and fluoride in addition to the appropriate electrolytes and CMC. MOI-STIR (Kingswood Co., Toronto) has a high sodium content and is mint flavored. SALUBE (Oraphorm Co., Australia) comes in small dropper bottles. SALIMENT (Richmond Pharm. Co., Ontario), also based on CMC, is lemon flavored. Xero-lube (Scherer Labs., Dallas, Texas), ARTISIAL (Jouvenal, Paris, France), and GLANDOSANE (Fresenius, Bad Homburg, West Germany) are available in ordinary spray bottles. Glycerine, hydroxyethylcellulose, and polyethylene oxides may also be found as bases for synthetic salivas.

Another broad approach to alleviating the manifold symptoms of xerostomia is to fit the mouth with a constant or controllable reservoir of synthetic saliva via a permanent or removable dental device. Palatal reservoirs require repeated refillings. A removable maxillary denture with reservoir rim is less cumbersome. It has several holes for filling with a syringe, drainage in use, and then washing after every meal. The removable denture with rim has space for about 3 ml of synthetic saliva. This denture, is expensive since custom-made, has an uncomfortable thickness, may hinder speech, and must be cleaned and refilled several times per day J.A. Toljanic in Quintessence of Dental Technology, June 1985, pp. 355-358 and The Journal of Prosthetic Dentistry, volume 52, No. 4, pp. 540-544 show pictures, give directions, and have a bibliography on this subject.

Several strong compounds with metabolic effects that is pharmaceuticals not foods, can stimulate production of saliva. These are generally administered in the form of tablets or capsules. They cannot be considered benign because unwanted side effects may occur. These compounds are cited in the background section, above. Constant ingestion of these drugs cannot be prudently advised.

One can stimulate the production of saliva by more or less constant sucking of soft candies, hard drops, pastilles, ascorbic acid tablets, bonbons, small pastries, soft drinks fruit juices, shredded coconut, and glasses of sweetened or acidulated water. This is cumbersome and can lead to a high rate of tooth decay.

Topical applications of glycerine, xylitol, carboxymethyl-cellulose, hydroxyethylcellulose, or other liquids or aqueous solutions of these compounds, which are more viscous than water, is preferable to repeatedly rinsing with water, because the higher viscosity of these humectants leads to less frequent applications.

The present invention is superior to all the other palatives and stimulants described above, because it stimulates all the salivary glands equally without the expense, bother, potential harm, or side effects of any of the known methods for alleviating xerostomia, no matter what the cause.

Firstly, the present invention utilizes a safe, mild, natural, food-acid of limited concentration which will give the resulting liquid a low enough pH to stimulate salivation. Food acids such as citric, lactic, malic, succinic, ascorbic; adipic, fumaric, and tartaric are preferred. Citric acid is most preferred.

Preferably the liquid or atomized spray of the present invention should be at a pH of from about 3 to about 4. This translates to a food-acid concentration from about 2 to about 3 wgt percent. The fruit acid stimulates the "sour" taste centers of the salivary system.

Secondly, a sweetener is employed in the solution or atomized spray of the present invention to stimulate salivation, yet it is known that the "sweet" centers are the same as the "bitter" centers of the salivary gland network of the mouth and tongue. The most common food-grade sweeteners are sugars such as glucose, dextrose, fructose, lactose, maltose, xylose, sucrose, corn sugar syrup, and other sweet mono- or di- saccharides. Ultimately, the word "sweet" is based on the taste sensations of professional taste panels. What a trained panel says is "sweet" is sweet. Normally, dilute solution of natural or synthetic compounds are further diluted and compared to very dilute solutions of sucrose. Then an arbitrary comparison such as "one-half" or "100 times" the sweetness of sucrose is given to the compound being tasted. Sucrose is the standard.

In the art of sialometry, the stimulation by different sweeteners is measured by comparing the amount of resting flow and stimulated flow at equal times under equal conditions. In one such set of tests on healthy, young adults the normal resting flow was found to be 0.34 ml/min. The data for stimulated flow for citric acid, three natural sugars and two artificial sweeteners for six minutes are found in Table I, along with the projected time to return to resting flow rate.

The data shown in Table I permit several generalizations, especially when the accepted "sweetness value" of fructose 1.1 and glucose 0.7, compared to sucrose at 1.0, are considered. Increasing molarity of all six stimulants leads to increasing salivary flow rates. The increases for the three sugars were linear with concentration and followed the "sweetness value". The "sour" acid stimulant alone was twice as effective as the "sweet" stimulant alone, but the rate of increase for the "sour" and the artificial sweeteners were asymptotic. Generally, the number of minutes for the return to the resting flow rate was about the same for all six stimulants.

The use of artificial sweeteners in the present invention is preferred over the use of saccharides because lesser concentrations are effective and the repeated use of sugars may cause dental caries in the patient. Sugars may be employed for edentulous individuals, however. The preferred concentration in a liquid or atomized spray of the present invention is from about 0.05 wgt percent to about 25 wgt percent for sugars.

TABLE I

Some Stimulated Flow Data for Salivation

| Stimulant | Molarity | Flow Rate (ml/min) | Return to Resting Flow Rate (min) |
|---|---|---|---|
| fructose | 0.29 | 0.57 | 6.8 |
| | 0.73 | 0.77 | 8.7 |
| | 1.17 | 0.97 | 8.7 |
| sucrose | 0.29 | 0.56 | 8.2 |
| | 0.73 | 0.67 | 7.7 |
| | 1.17 | 0.74 | 6.3 |
| glucose | 0.29 | 0.48 | 7.3 |
| | 0.73 | 0.43(sic) | 6.7 |
| | 1.17 | 0.52 | 6.7 |
| Aspartame | 0.002 | 0.52 | 5.7 |
| | 0.004 | 0.66 | 6.9 |
| | 0.008 | 0.70 | 6.9 |
| | 0.017 | 0.81 | 7.8 |
| | 0.034 | 0.82 | 6.8 |
| saccharin, sodium | 0.001 | 0.50 | 6.5 |
| | 0.002 | 0.54 | 6.8 |
| | 0.04 | 0.78 | 8.0 |
| | 0.08 | 0.87 | 8.7 |
| | 0.21 | 0.94 | 9.0 |
| | 0.42 | 1.04 | 10.5 |
| citric acid | 0.026 | 0.93 | 7.1 |
| | 0.052 | 1.13 | 7.2 |
| | 0.13 | 1.67 | 7.1 |
| | 0.26 | 1.68 | 7.3 |

Certain commercial sweeteners are mixtures of both synthetic and natural compounds in order .to overcome the aftertaste of synthetic sweeteners. It is believed that SWEET & LOW is a mixture of saccharin and dextrose (glucose) sugar, and that EQUAL is a mixture of ASPARTAME dipeptide and dextrose (glucose) or lactose. These mixtures are useful in practicing the present invention, even though the sugar content is potentially cariogenic. They do help overcome any unpleasant aftertaste. More preferable for the sweetener of the present invention is a synthetic sweetener containing a compound to overcome any unpleasant aftertaste, which is not cariogenic. Most preferable for this purpose is a synthetic sweetener plus a non-sugar, sugar-related compound (an alcohol sugar) such as sorbitol, xylitol, mannitol, maltilol, and hexitol, or starch hydrolysate such as Lycasin, or the like, of which sorbitol is most preferred. These and similar hydroxy compounds overcome any unpleasant aftertaste of synthetic sweeteners without being cariogenic.

In fact, there are many synthetic compounds much sweeter than sucrose, according to taste panels. Their general use is contemplated by this invention, especially if the compounds are cleared for human consumption by The U.S. Food and Drug Administration. Selected highly "sweet" synthetic compounds are illustrated, but not limited, by those found in Table II. The molecular structure of many other synthetic sweeteners will be known to those skilled in the art. In the present invention saccharin or Aspartame to which sorbitol or mannitol has been added is the preferred sweetener.

TABLE II

Sweetness Values of Some Synthetic Compounds

| Compound | "Sweetness" Times Sucrose |
|---|---|
| N-(L-aspartyl)-N'-[(2,2,5,5 tetramethylcyclopentyl)carbonyl]-(S)-1,1 diaminoethane | 600–800 |
| L-aspartyl-1,1-diaminodycyclopentyl-methane | 500–700 |
| L-aspartyl-1,1-diaminotetramethylcyclopentane | 800–1000 |
| L-aspartyl-1,1-diaminotetramethylcyclopentane as the 1.5 hydrate | 600–800 |
| L-aspartyl-1,1-diaminodimethylcyclopentane | 300–400 |
| L-aspartyl-1,1-diaminomethylcyclohexyl | 150–250 |
| tripeptides: Asp-D-Ala-1-aminocycloalkane OCH3 where cycloalkane is $C_3$ to $C_6$ | 20 |
| trifluoroacetyl-L-aspartyl-p-cyanoanilide | 3000 |
| trifluoroacetyl-L-aspartyl-p-nitroanilide | 1500 |
| trifluoroacetyl-L-aspartyl-p-chloroanilide | 120 |
| L-aspartyl-L-phenylalanine methyl ester (Aspartame) | 160 |
| L-aspartyl-L-hexylalanine methyl ester | 225 |
| L-aspartyl-aminomalonic methyl fenchyl ester | 27000 |
| L-aspartyl-aminomalonic methyl trans-2-methyl cyclohexyl ester | 6400 |
| L-aspartyl-aminomalonic methyl cyclohexyl ester | 700 |
| ammonium 1,2-benzisothiazol-3-one (ammonium saccharin) | 500 |
| sodium 1,2-benzisothiazol-3-one (sodium saccharin) | 400 |

Because it is generally considered that a pH of 5.5 and below is potentially harmful to human teeth, in order to ensure stability of the teeth during long-term, repeated use of the liquid or atomized spray of the instant invention, the aqueous medium for the saliva stimulants is saturated calcium phosphate. This saturated solution by the general principles of aqueous equilibrium in chemistry minimizes any erosion, pitting, corrosion, or attack of the teeth by the salivary stimulant. There are at least five calcium phosphates: monocalcium phosphate [$CaH_4(PO_4)_2$] dicalcium phosphate [$Ca_2H_4)_2$], octacalcium phosphate [$Ca_4(PO_4)_3OH$], tricalcium phosphate [$Ca_3(PO)_4)_2$] and hydroxyapatite [$Ca_5(PO_4)_3OH$]. In aqueous solution all the possible ions will be in equilibrium with the relative amounts of the various ions determined by the pH. At the pH of about 3 to about 4 most favored for this invention, the calcium and phosphorus contents are about 0.6 wgt percent calcium and about 2.3 wgt percent phosphorus. Teeth kept in this saturated calcium phosphate solution will remain undamaged indefinitely. It is preferable to prepare the solution of the present invention with monocalcium phosphate, because it is moderately soluble in water and is often used as a supplement in foods. The liquid solution of the present invention may be carried and dispensed by a variety of means. It may be carried in any manner of bottle, flask, or container for alleviating xerostomia by drinking, rinsing, gargling, or topical application, all with or without expectoration. A flask of any size may be fitted with a hand-activated or bulb-activated spray pump for directing a stream into the mouth. Obviously, the finer the stream, the longer the supply will last. A means of pumping a fine stream into the mouth is preferable merely to using a bottle or flask as a liquid reservoir. It is most highly preferred to use a metering, hand-actuated, aerosol spray bottle for administration of an atomized colloidal droplet spray, because swallowing sialogogue should be minimized.

A so-called "atomizer" breaks up a stream or "shot" of liquid into a colloidal aerosol. This aerosol has such a high surface area that the colloid of liquid phase in air takes on the properties of a gas to some extent. That is, the colloidal aerosol stays suspended much longer than liquid drops would before falling. Furthermore, a colloidal aerosol will diffuse throughout a gaseous volume rather than coalesce in order to minimize its surface. For the present invention, an aerosol is ideal.

The atomized aerosol spray of the present invention may be hand-pumped through the properly small-sized orifice, sprayed under the pressure of gas such as air, carbon dioxide or isobutane, or be "atomized" by packaging under its own pressure. In any case, the colloidal droplets easily diffuse to all areas of the mouth to stimulate all the types of locales of salivary glands, for a minimal amount of stored liquid. The atomizer may be metered to deliver any desired amount of aerosol employing from about 0.05 to about 2 ml. The preferred amount of liquid to be transformed into a aerosol mist dose per actuation of the aerosol head is about 0.1 to about 0.4 ml. The most preferred aerosol dose per actuation employs about 0.15 ml liquid stimulant. A reniform spray is most preferred.

An aerosol spray, especially a metered one, obviates any pain or trauma or effort by a seriously afflicted patient in chewing tablets, chewing gum, topically applying, rinsing or gargling, or expectorating. Many patients with xerostomia have sores, fissures, inflammation, desiccated or eroded areas, tumors, and the like for which an aerosol spray is the most benign means of contact to stimulate salivation. Even at one reniform metered dose of aerosol a minute, a severely afflicted person could go about his affairs all day carrying a 50–75 ml aerosol container, easily carried in a pocket or purse.

Many other embodiments of the present invention are apparent to those skilled in the art. The protection sought for this invention by grant of Letters Patent is broadly described in the claims below:

We claim:

1. In combination, a spray head and an aqueous sialogogue for the alleviation of xerostomia comprising:
   means for generating a reniform spray form, said reniform spray form coinciding with the location of the salivary glands in the human mouth,
   said reniform spray generation means consisting of a plurality of orifices in said spray head;
   said aqueous sialogogue comprising:
   a) from about 2 to 3 weight-percent of food-grade organic acidulant;
   b) a food-grade sweetener benign to stomic microflora selected from the group consisting of a sugar, a synthetic sweetener, a reduced sugar-related compound, and mixtures thereof; and
   c) a saturated calcium phosphate solution,
   whereby production of human saliva is promoted without corrosion, infection, or dissolution of human teeth.

2. The combination of claim 1, wherein said plurality of orifices consists of an arcuate array of orifices in said spray head from about the 9 o'clock position to about the 3 o'clock position.

3. The combination of claim 1, wherein said plurality of orifices consists of orifices located at and only at the 10, 12, and 2 o'clock positions.

4. The combination of claim 1, wherein said plurality of orifices consists of orifices located at and only at the 9, 12, and 3 o'clock positions.

5. The combination of claim 1, wherein said plurality of orifices consists of orifices located at and only at the 9, 12, 3, and 6 o'clock positions.

6. The combination of claim 1, wherein said plurality of orifices consists of orifices located at the 10, 10:30, 11, 11:30, 12, 12:30, 1, 1:30, and 2 o'clock positions.

7. The combination of claim 6, wherein said plurality of orifices further consists of an orifice at the 6 o'clock position.

8. The combination of claim 1, wherein said plurality of orifices consists of three orifices.

9. The combination of claim 8, wherein said three orifices are located in a triangular array.

10. The combination of claim 9, wherein said triangular array consists of one larger upper orifice and two smaller lower orifices.

11. The combination of claim 1, wherein said spray head has an outline and said plurality of orifices are in an arcuate array approximately parallel to said outline.

12. The combination of claim 11, wherein said plurality of orifices further consists of an orifice opposite said arcuate array.

13. The combination of claim 1, wherein said plurality of orifices includes an arcuate orifice.

14. The combination of claim 13, wherein said plurality of orifices consists of said arcuate orifice and an orifice opposite said arcuate orifice.

15. The combination of claim 1, wherein said plurality of orifices consists of four orifices in a diamond array.

* * * * *